United States Patent
Fokow et al.

(10) Patent No.: US 10,613,057 B2
(45) Date of Patent: Apr. 7, 2020

(54) DEVICE AND METHOD FOR EXAMINING MATERIALS BY MEANS OF ACOUSTIC SPECTROSCOPY

(71) Applicant: E3 TECHNOLOGY SP. Z O.O., Warsaw (PL)

(72) Inventors: Krzysztof Fokow, Warsaw (PL); Miroslaw Wrobel, Karlstadt (DE)

(73) Assignee: E3 TECHNOLOGY SP. Z O.O., Warsaw (PL)

( * ) Notice: Subject to any disclaimer, the term of this patent is extended or adjusted under 35 U.S.C. 154(b) by 112 days.

(21) Appl. No.: 15/743,404

(22) PCT Filed: Jun. 16, 2016

(86) PCT No.: PCT/EP2016/063868
§ 371 (c)(1),
(2) Date: Jan. 10, 2018

(87) PCT Pub. No.: WO2017/012794
PCT Pub. Date: Jan. 26, 2017

(65) Prior Publication Data
US 2018/0266996 A1 Sep. 20, 2018

(30) Foreign Application Priority Data

Jul. 17, 2015 (EP) ..................................... 15177198
Oct. 26, 2015 (DE) .................... 20 2015 105 692 U
Feb. 8, 2016 (DE) ........................ 10 2016 102 131

(51) Int. Cl.
*G01N 29/024* (2006.01)
*G01N 29/032* (2006.01)
(Continued)

(52) U.S. Cl.
CPC ............. *G01N 29/024* (2013.01); *G01N 9/24* (2013.01); *G01N 29/032* (2013.01); *G01N 29/07* (2013.01);
(Continued)

(58) Field of Classification Search
CPC .... G01N 29/024; G01N 29/032; G01N 29/24; G01N 29/07; G01N 29/11; G01N 29/30; G01N 29/46
See application file for complete search history.

(56) References Cited

U.S. PATENT DOCUMENTS 3,184,969 A * 5/1965 Bolton ................ G01F 23/2962
367/902
4,364,273 A * 12/1982 Redding ................ G01N 29/11
367/101
(Continued)

FOREIGN PATENT DOCUMENTS

| DE | 19841154 A1 | 4/2000 |
|---|---|---|
| DE | 10324990 B3 | 11/2004 |
| DE | 102008014300 A1 | 9/2009 |
| WO | 2009083050 A1 | 7/2009 |

OTHER PUBLICATIONS

Ju, et al., Simultaneous Measurement of Local Longitudinal and Transverse Wave Velocities, Attenuation, Density, and Thickness of Films by Using Point-Focus Ultrasonic Spectroscopy, Journal of Applied Physics, 2012, 112: 084910-1 thru 084910-8.
(Continued)

*Primary Examiner* — Helen C Kwok
(74) *Attorney, Agent, or Firm* — Quarles & Brady LLP (57) ABSTRACT

A device for examining a test material via acoustic spectroscopy, including a measuring distance which is formed from a reference material and the test material an ultrasonic transmission device for transmitting an ultrasonic transmission signal having an initial amplitude (A0) through the
(Continued)

measuring distance, a first ultrasonic reception device for receiving the transmitted ultrasonic reception signal after the signal has passed through the measuring distance, and a second ultrasonic reception device for receiving the ultrasonic receiving signal reflected on the boundary surface between the test material and the reference material after the signal has twice passed through the reference material or test material, the transmission device being configured for giving ultrasonic transmission signals having different frequencies (f) and the two reception devices being configured for receiving corresponding ultrasonic reception signals having different frequencies.

19 Claims, 4 Drawing Sheets

(51) Int. Cl.
  *G01N 29/30* (2006.01)
  *G01N 29/11* (2006.01)
  *G01N 29/07* (2006.01)
  *G01N 29/46* (2006.01)
  *G01N 9/24* (2006.01)
  *G01N 33/28* (2006.01)
(52) U.S. Cl.
  CPC ............. *G01N 29/11* (2013.01); *G01N 29/30* (2013.01); *G01N 29/46* (2013.01); *G01N 33/2847* (2013.01); *G01N 2291/0226* (2013.01); *G01N 2291/045* (2013.01); *G01N 2291/048* (2013.01)

(56) References Cited

U.S. PATENT DOCUMENTS

| | | | | |
|---|---|---|---|---|
| 4,380,929 A | * | 4/1983 | Taszarek | G01B 17/02 73/579 |
| 4,391,142 A | * | 7/1983 | Cantrell, Jr. | G01S 7/5276 73/602 |
| 4,624,142 A | * | 11/1986 | Heyman | G01H 5/00 367/99 |
| 4,677,842 A | * | 7/1987 | Piche | G01N 9/24 73/32 A |
| 4,991,124 A | * | 2/1991 | Kline | G01N 9/24 250/301 |
| 5,433,112 A | * | 7/1995 | Piche | G01N 29/024 73/54.41 |
| 6,651,484 B2 | * | 11/2003 | Fiebelkorn | G01N 29/02 310/336 |
| 8,813,559 B2 | * | 8/2014 | Welle | G01F 23/2962 73/290 V |
| 9,003,894 B2 | * | 4/2015 | Sui | G01F 1/662 73/861.18 |
| 2006/0028096 A1 | * | 2/2006 | Kushibiki | G01N 25/16 310/319 |
| 2015/0059442 A1 | * | 3/2015 | Liljenberg | G01N 29/032 73/24.01 |

OTHER PUBLICATIONS

PCT International Search Report, PCT/EP2016/063868, dated Sep. 22, 2016.
PCT English Language Translation of the International Preliminary Report on Patentability, PCT/EP2016/063868, dated Feb. 1, 2018.

* cited by examiner

Acoustic pressure: $P(x, t) = P_0 \cdot e^{-\alpha \cdot x} \cdot \sin(2\pi f (t - x/c))$ Attenuation: $A(x) = A_0 \cdot e^{-\alpha \cdot x}$ Impedance: $Z = c \cdot \rho$ Compressibility: $K = Z \cdot c = c^2 \rho$ Reflection and Transmission: $R = \dfrac{Z_A - Z_B}{Z_A + Z_B}$, $T = 1 - R = \dfrac{2 \cdot Z_B}{Z_A + Z_B}$

Fig. 3

$$Z_M = Z_R \cdot \frac{1-R}{1+R} = Z_R \cdot \frac{A_0 - A_R \cdot e^{2\alpha R \times R}}{A_0 + A_R \cdot e^{2\alpha R \times R}}$$

$$R = \frac{Z_R - Z_M}{Z_R + Z_M} \quad A = \frac{A_R \cdot e^{2\alpha R \times R}}{A_0}$$

$$\alpha_M = -\frac{1}{x_M} \cdot \ln \frac{A_2^{(T)} \cdot e^{2\alpha R \times R}}{A_0 \cdot T} = -\frac{1}{x_M} \cdot \ln \frac{A_T \cdot e^{2\alpha R \times R}}{A_0 \cdot (1-R)}$$

$$c_M = \frac{x_M}{t_M} = \frac{x_M}{t_G - t_R} = \frac{x_M}{t_G - \frac{x_G}{c_R}} = \frac{x_M}{t_G \cdot c_R - x_G} \cdot c_R$$

$$\rho_M = \frac{Z_M}{c_M} = \frac{Z_M(f)}{c_M(f)}$$

$$K_M = \rho_M \cdot c_M^2 = \begin{bmatrix} \rho_{M,1} \cdot c_{M,1}^2 \\ \rho_{M,2} \cdot c_{M,2}^2 \\ \vdots \\ \rho_{M,2} \cdot c_{M,H}^2 \end{bmatrix} = \begin{bmatrix} Z_{M,1} \cdot c_{M,1} \\ Z_{M,2} \cdot c_{M,2} \\ \vdots \\ Z_{M,2} \cdot c_{M,H} \end{bmatrix}$$

Fig. 4

DEVICE AND METHOD FOR EXAMINING MATERIALS BY MEANS OF ACOUSTIC SPECTROSCOPY

CROSS-REFERENCE TO RELATED APPLICATIONS

This application represents the national stage entry of PCT International Application No. PCT/EP2016/063868 filed on Jun. 16, 2016, which claims the benefit of European Patent Application No. 15177198.7 filed on Jul. 17, 2015 and German Patent Application No. 20 2015 105 692.3 filed on Oct. 26, 2015, and German Patent Application No. 10 2016 102 131.8 filed Feb. 8, 2016, the entire contents of which are incorporated herein by reference for all purposes.

The invention relates to a device and a method for examining materials via acoustic spectroscopy according to the preamble of claim 1.

A device for examining liquid or gaseous media via acoustic spectroscopy is known, for example, from DE 103 24 990 B3. In this device, a transmission device for transmitting several transmission signals having different frequencies and a reception device for receiving corresponding reception signals are provided. Using a processing device, the phase shift for each signal pair consisting of the transmission signal and the reception signal can be identified and a value qualifying the examined medium can be derived by means of the phase shift. In the described device, signal packages having different frequencies are transmitted consecutively in direct sequence. The frequencies preferably move in a range from 1 to 15 MHz, with each signal package preferably comprising at least 100 periods. The specific reception signals are captured for each signal package and thus for each frequency step via the reception device and are then directed to a processing device. In the processing device, the phase-shift angle which is arranged between the two signals and which is caused by the passage through the examined medium is identified for each frequency-specific signal pair consisting of the transmission signal and the reception signal. Thus, a plurality of different frequency-specific phase-shift values is ultimately captured via this frequency-specific sampling of the medium, the number of the phase-shift values depending on the number of signal pairs consisting of the transmission signal and the reception signal. In this manner, information on the behavior of the medium can be gathered from a very large frequency range defined via individual frequency steps, said information allowing to draw conclusions on the properties of the examined medium. Due to the frequency-specific sampling of the medium and the corresponding determination of the frequency-related phase angles, the medium can be examined much more specifically since a change of the medium has a different impact on the corresponding frequency-specific signal pair consisting of the transmission signal and the reception signal.

A disadvantage of the device described in DE 103 24 990 B3 is that it is based upon the evaluation of the values of the phase-shift which is caused by the passage of the transmission signal through the material to be examined and is documented via the reception signal. For the evaluation of the phase shift between the transmission signal and the reception signal can lead to undesired losses of information by which the evaluation result is significantly falsified. These losses of information are caused by the fact that the value of the phase shift is limited to a value range between 0° and 360°. Should, however, the phase shift between the transmission signal and the reception signal be greater than 360°, the method described in said document yields a phase-shift value which cannot be clearly allocated. Should the phase shift between the transmission signal and the reception signal be 400°, for example, the evaluation device described in said document yields a phase-shift value of 40°. The evaluation results derived therefrom are thus crucially falsified and unusable since the evaluation yields results which are equivalent to a phase shift of 40° and not to a phase shift of 400° (=360°+40°).

In order to solve this problem, in which results cannot be clearly allocated when evaluating the phase shift between a transmission signal and a reception signal, document DE 198 41 154 A1 proposes generating transmission signals having different frequencies. In this context, the different frequencies serve as a type of nonius when assessing the phase shifts. Thus it is possible to clearly allocate the measured phase-shift values to the actual phase shift between the transmission signal and the reception signal. However, this method has the disadvantage that the sound waves in the medium to be examined are transmitted with different speeds of sound depending on the corresponding transmission frequency, these different transmission speeds possibly leading to crucial measurement errors in the medium to be examined. The dependence of the speed of propagation of the transmission signal on the corresponding transmission frequency is described by the Kramers-Kronig relation. In this respect, the measuring method according to DE 198 41 154 A1 has proven to be unsuitable since the measurement errors cannot be taken into account due to the inconsistent speed of propagation of the sound waves in dependence on the corresponding transmission frequency.

The principles of acoustic spectroscopy, which form the basis of the device according to the invention, are described, though by no means exclusively, in the following reference books, for example:

Reference book 1: *Molekularakustik* [Molecular Acoustics], Werner Schaaffs, published by Springer Verlag, 1963 (ISBN-10:3642491413, ISBN-13:978-3642491412)

Reference book 2: *Molecular Acoustics/Molekularakustik*, K.-H. Hellwege, A. M. Hellwege, W. Schaaffs, published by Springer Verlag, 1967 (ISBN-10:3540038973, ISBN-13:978-3540038979)

Reference book 3: *Molecular Acoustics*, A. J. Matheson, John Wiley & Sons Publishers, 1971 (ISBN-10: 1861561857, ISBN-13:978-1861561855)

Reference book 4: *Werkstoffprüfung mit Ultraschall* [*Testing Materials using Ultrasound*], Josef Krautkramer, Herbert Krautkramer, published by Springer-Verlag, 1975

Starting from this state of the art, a device and a method for examining test materials via acoustic spectroscopy are to be proposed. In particular, a method and a device are to be proposed, by means of which the material properties of operating materials, in particular transformer oils, are to be examined online.

Transformers serve for converting an AC input voltage into an AC output voltage, the electrical energy having to be transmitted between two coils via magnetic fields. When AC input voltages and AC output voltages are very high, transformers are generally utilized whose housings are filled with transformer oil in order to ensure a sufficient insulation and cooling between the transmitter coils. Since the transformer oil is highly hygroscopic, it tends to take up water over time, the water being converted to acids in the transformer oil. Due to the water or rather the acid in the transformer oil, the functionality of the transformer is increasingly impaired over time since the electric insulation, which is ensured by the transformer oil and can be indicated as a type of maximal breakdown voltage, for example, is diminished due to the water or the acid. In known transformers, it is therefore common practice to exchange or regenerate the transformer oil in regular servicing cycles so as to reliably ensure the functionality of the transformer.

This regular exchange of the transformer oil, however, is extraordinarily cumbersome and expensive since the transformer oil contains highly poisonous ingredients and therefore the disposal or recycling of said transformer oil is complicated. Furthermore, if the servicing cycles are chosen too far apart so as to keep the costs for exchanging the transformer oil as low as possible, the transformer can fail completely.

Known methods for examining the transformer oil presuppose that the transformer must be opened and a sample of the transformer oil must be taken. Opening the transformer for taking a sample, however, is highly problematic since the transformer oil is highly hygroscopic and a relatively large amount of water molecules will get into the transformer oil from the surrounding air when opening the transformer housing.

The object of the invention at hand is therefore to propose a device and a method for examining materials, in particular oil such as transformer oil, via acoustic spectroscopy, by means of which the above mentioned disadvantages are avoided.

The object is attained by a device, a method and a transformer according to the teachings of the independent claims.

Advantageous embodiments of the invention are the subject matter of the dependent claims.

The device according to the invention comprises a measuring distance which is formed from a reference material and the actual test material to be examined. The object of the examination is to identify the acoustic material parameters of the test material. The acoustic material parameters of the reference material, in particular the density, the sonic transmission speed, the acoustic attenuation coefficient and/or the acoustic impedance of the reference material, are known for different frequencies. Furthermore, the length of the reference material and the length of the test material, through which the ultrasonic signals pass during the examination, are known from the geometry of the measuring distance.

According to the generic state of the art, the device comprises an ultrasonic transmission device for transmitting ultrasonic transmission signals having an initial amplitude $A_0$ through the measuring distance. Furthermore, the device comprises a first ultrasonic reception device by means of which the transmitted ultrasonic reception signals can be received and measured after passing through the measuring distance. Other than the first ultrasonic reception device, the device comprises a second ultrasonic reception device for receiving the ultrasonic reception signals reflected on the boundary surface between the test material and the reference material after said signals have twice passed through the reference material or the test material. The second ultrasonic reception device can also be realized via correspondingly switching the ultrasonic reception device, if needed.

The transmission device as well as the two reception devices are suitable for transmitting or receiving, respectively, ultrasonic signals having different frequencies in order to be able to carry out a multispectral ultrasonic examination of the test material with different transmission frequencies and reception frequencies.

In contrast to the teachings of DE 103 24 990 B3, however, the phase shift is not determined for every signal pair consisting of the transmission signal and the reception signal when evaluating the signals. Instead, the time of flight of the allocated transmitted ultrasonic reception signal is measured in a first processing device for every transmission signal after said signal has entirely passed through the measuring distance. Moreover, the amplitude of the allocated transmitted ultrasonic reception signal is identified for every transmission signal, after said signal has passed through the measuring distance, using a second processing device, and the amplitude of the allocated ultrasonic reception signal reflected on the boundary surface between the test material and the reference material is identified for every transmission signal after said signal has twice passed through the reference material or the test material, respectively, using a third processing device. Subsequently, the acoustic material parameters of the test material for different frequencies, in particular the density, the sonic transmission speed, the acoustic attenuation value and/or the acoustic impedance of the test material, are calculated in an evaluation device from the three measuring values identified by means of the processing devices, namely the time of flight, the amplitude of the transmitted ultrasonic reception signal and the amplitude of the reflected ultrasonic reception signal. The amplitude of the transmitted ultrasonic reception signal or the amplitude of the reflected ultrasonic reception signal, respectively, can be directly measured or can be identified by determining other measuring values, e.g. the signal attenuation, and the subsequent derivation of the amplitude values.

According to the invention, the measuring errors known from the state of the art, such as they occur in the usage of the phase shift between the transmission signal and the reception signal, are avoided by directly measuring the time of flight of the transmitted ultrasonic reception signal after said signal has passed through the measuring distance.

Examinations on test materials, such as on transformer oils, upon subjection of said materials to ultrasonic signals and subsequent identification of the time of flight, the amplitude of the transmitted reception signal and the amplitude of the reflected reception signal, have shown that changes in the test material are significantly depicted in the results datasets yielded from the time of flight, the transmission amplitude and the reflection amplitude. The conventional acoustic spectroscopy, in which so far merely the signal attenuation has been measured, is thus enhanced according to the invention to the extent that not only the specific and frequency-dependent attenuation, i.e. the relation between the input amplitude and the transmission amplitude or the relation between the input amplitude and the reflection amplitude, is determined for every frequency but that the specific and frequency-dependent time of flight (TOF) is determined as well. By measuring the time of flight, in particular the dispersivity of the examined material can be identified. The combination of measuring the attenuation and the dispersivity of the examined test material allows a highly differentiated characterization of the examined test material.

In contrast to the previous examination methods, it is no longer the phase shift which is measured but rather the time of flight of the ultrasonic signal itself is measured by means of the device according to the invention. In order to be able to determine the properties of the examined materials using an adequate resolution, it is particularly advantageous if the time of flight can be identified with a resolution of at least 100 picoseconds in the first processing device. The time of flight should preferably be able to be identified with a resolution of at least 10 picoseconds.

Which time measuring device is provided in the first processing device for determining the time of flight is generally arbitrary. In order to attain resolutions in particular in the range of below 100 picoseconds when measuring the time of flight, it is particularly advantageous if so-called time-to-digital converters are used for this purpose. These time-to-digital converters are electronic component groups which can measure temporal intervals in the range of <100 picoseconds and convert them to a digital version. Measuring time is based upon the known time of flight of an electric signal through the component groups of the time-to-digital converter. In this context, the time of flight is determined by how many of the electrical circuits having a known time of flight between emitting the transmission signal on the one hand and receiving the input signal on the other hand are passed through. This number of passages through electronic component groups having a known time of flight is then counted, the measured time of flight then corresponding to the multiplication of the known time of flight of an individual circuit by the number of passages.

The ultrasonic reception signals are received by means of the second ultrasonic reception device, said ultrasonic reception signals first being reflected on the boundary surface between the test material and the reference material after emitting the ultrasonic transmission signal having an initial amplitude and after passing through the test material or the reference material and subsequently passing through the test material or reference material a second time. The geometric arrangement of the second ultrasonic reception device therefore exactly corresponds to that part of the measuring distance on which the ultrasonic transmission device is also arranged. For reducing the device-related expenditure, it is therefore particularly advantageous if the second ultrasonic reception device is realized by switching the ultrasonic transmission device. In other words, this means that, during operation of the device, the ultrasonic transmission signal is first generated using the ultrasonic transmission device and is then emitted into the measuring distance. Subsequently, the ultrasonic transmission device is switched so that it functions as an ultrasonic reception device. The ultrasonic transmission signal initially passes through the reference material or the test material a first time and is subsequently reflected on the boundary surface between the test material and the reference material. The reflected ultrasonic signal then passes through the reference material and the test material a second time and then finally returns to the beginning of the measuring distance where it can be received and measured by the ultrasonic transmission device, which in the switched state functions as an ultrasonic reception device From which material the reference material of the measuring distance is produced is generally arbitrary. It is particularly advantageous if the reference material consists of a solid body, in particular plastic or glass.

If the test material to be examined is also a solid body, a test piece, whose length is exactly determined, must be produced from the test material for carrying out the examination. This test body can be joined together with the reference body from the reference material and can be inserted between the ultrasonic transmission devices or ultrasonic reception devices, respectively. Liquid or gaseous test materials, however, can also be examined using the device according to the invention. For this purpose, a cavity is formed between the boundary surface of the reference material and the first ultrasonic reception device. The length of this cavity between the boundary surface on the one hand and the ultrasonic reception device on the other hand must be precisely determined. During the actual examination, this cavity is filled with the liquid or gaseous test material and the actual measurement is carried out. Alternatively, it is also conceivable for the liquid or gaseous test material to flow through the cavity during the examination.

For which purpose the device according to the invention is used is generally arbitrary. The device is particularly advantageous for online measurements of oil or other operating materials which must regularly be exchanged. For via the online measurement of the oil or the operating material, the oil or the operating material can be exchanged in dependence on wear and the disadvantages of servicing having to be carried out at regular intervals can thus be avoided. The device according to the invention can be very aptly used in particular for assessing the state of transformer oil. For this purpose, the invention is connected to a container in which the oil or the operating material which is to be assessed, in particular the transformer oil, is contained. During the actual examination, the oil or the operating material from the container fills or flows through the cavity between the boundary surface of the reference material and the first ultrasonic reception device. Via the multispectral examination of the oil or operating material, the density, the sonic transmission speed, the acoustic attenuation coefficient or the acoustic impedance of the oil or operating material are identified.

As far as transformer oil is examined using the device according to the invention, it is particularly advantageous if the water content or the acidity level in the transformer oil is subsequently derived from the acoustic material parameters of the transformer oil. For these two parameters provide information on the aging of the transformer oil and can be utilized to the extent that the transformer oil is to be exchanged only after reaching a predetermined aging degree, measured by the water content or the acidity level.

In regard of the particularly advantageous assessment of transformer oil, to a transformer is moreover proposed for converting an AC input voltage to an AC output voltage, said transformer being filled with transformer oil and comprising a device according to the invention for examining the transformer oil online.

The method according to the invention, in turn, is characterized by the determination of the time of flight of the transmitted ultrasonic reception signal, the amplitude of the transmitted ultrasonic reception signal and the amplitude of the ultrasonic reception signal reflected on the boundary surface between the test material and the reference material. Using these two measuring values, the specific acoustic material parameters of the test material are calculated for different frequencies, in particular the density, the sonic transmission speed, the acoustic attenuation coefficient and/or the acoustic impedance.

Which type of ultrasonic waves are utilized for examination by means of the method according to the invention or the device according to the invention is generally arbitrary. Longitudinal ultrasonic waves in the lower megahertz range are particularly suitable. Furthermore, it is conceivable for the ultrasonic wave signals having different frequencies to be consecutively emitted from the ultrasonic transmission device individually or as groups.

Alternatively, the ultrasonic transmission signal can also be modulated onto and emitted from a shared carrier signal for the different frequencies by means of the ultrasonic transmission device. It is also conceivable for the ultrasonic transmission signal having different frequencies and the ultrasonic transmission device to be added to a shared carrier signal as a superposition and to be emitted together.

In the following, the invention is described in an exemplary manner by way of an embodiment schematically illustrated in the drawings.

In the figures.

Figure 1:
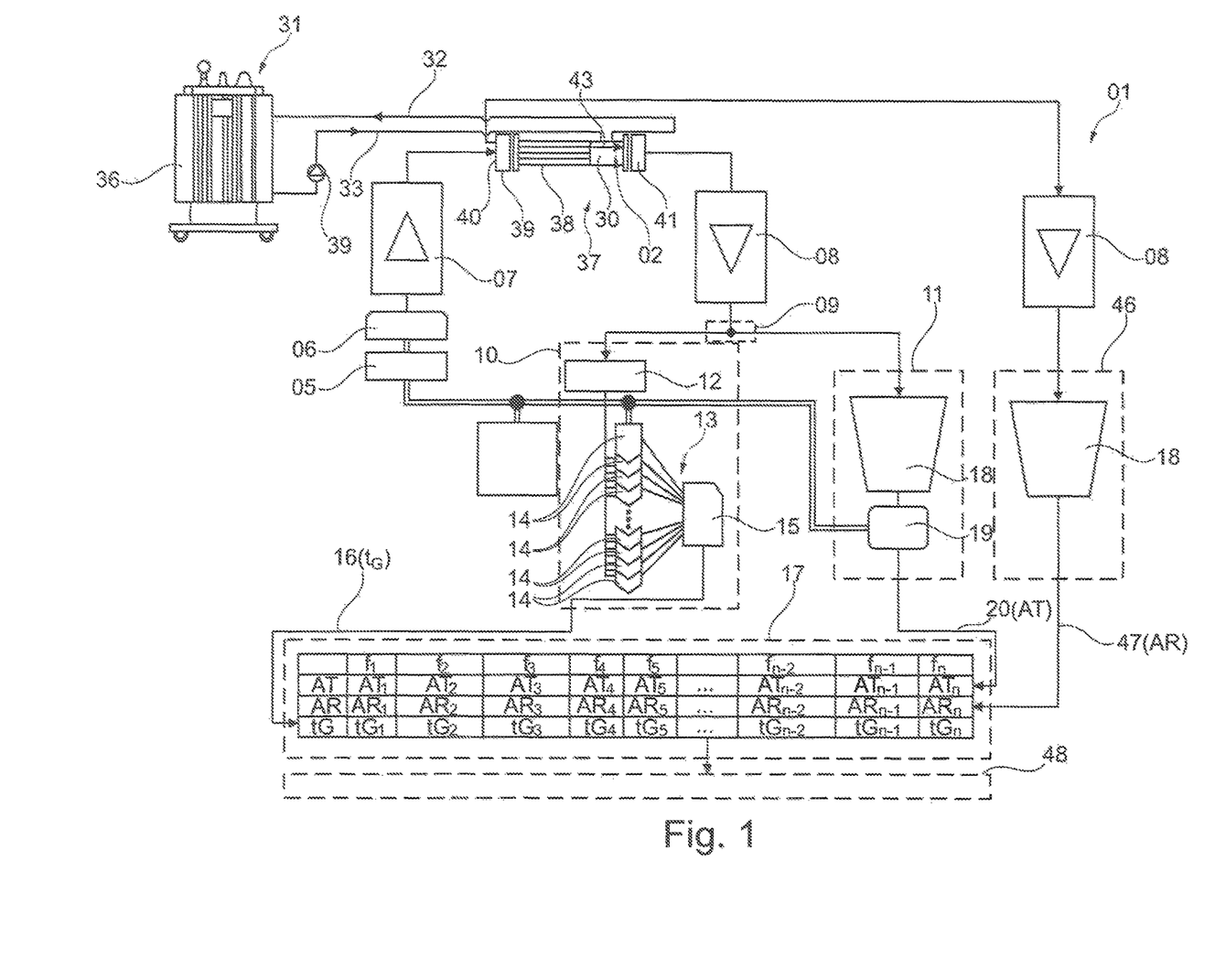
FIG. 1 illustrates a device according to the invention having different functional modules in a schematic diagram.

FIG. 1 illustrates in a schematic diagram the basic setup of a device 01 according to the invention, as it can be utilized for the online examination of a test material 02. The test material 02 is a transformer oil 30 (cf. FIG. 2) from a transformer 31. A cavity 35 is connected to the transformer 31 via connecting tubes 32 and 33 and via an operation of a pump 34 so that the transformer oil 30 can be pumped from the inside of the housing 36 in circulation through the cavity 35.

The setup of the measuring distance 37 when carrying out the actual examination of the test material 02 is to be briefly described in the following by way of the sketch in FIG. 2.

The measuring distance 37 consists, on the one hand, of a reference material 38 and the test material 02 to be examined, which is the transformer oil 30 in the illustrated embodiment. The reference material 38 can be a solid body made of glass or plastic, for example, the acoustic material properties of the reference material 38, i.e. the acoustic attenuation coefficient $\alpha_R$, the acoustic impedance $Z_R$, the density $\rho_R$, the sonic transmission speed $c_R$, having to be at least partially known. Moreover, the length $x_R$ of the reference material 38 and the length $x_M$ of the test material, i.e. the clear span of the cavity 35 in the signal direction, are known.

An ultrasonic transmission device 39, by means of which ultrasonic transmission signals can be generated having an initial amplitude $A_0$ and can be coupled into the measuring distance, is arranged at the beginning of the measuring distance 37. The ultrasonic transmission device 39 is a combined apparatus which can also function as an ultrasonic reception device 40 by being switched. An ultrasonic reception device 41, by means of which ultrasonic signals can be received, is also arranged at the end of the measuring distance.

During the actual examination of the test material 02, the transformer oil 30 first flows through the cavity 35 via the operation of the pump 34. In this context, the transformer oil can be measured online without having to open the housing 36. As soon as the cavity 35 is completely filled with transformer oil 30, the ultrasonic transmission device 39 generates an ultrasonic transmission signal having an initial amplitude $A_0$ and couples said transmission signal into the measuring distance 37.

Figure 2:
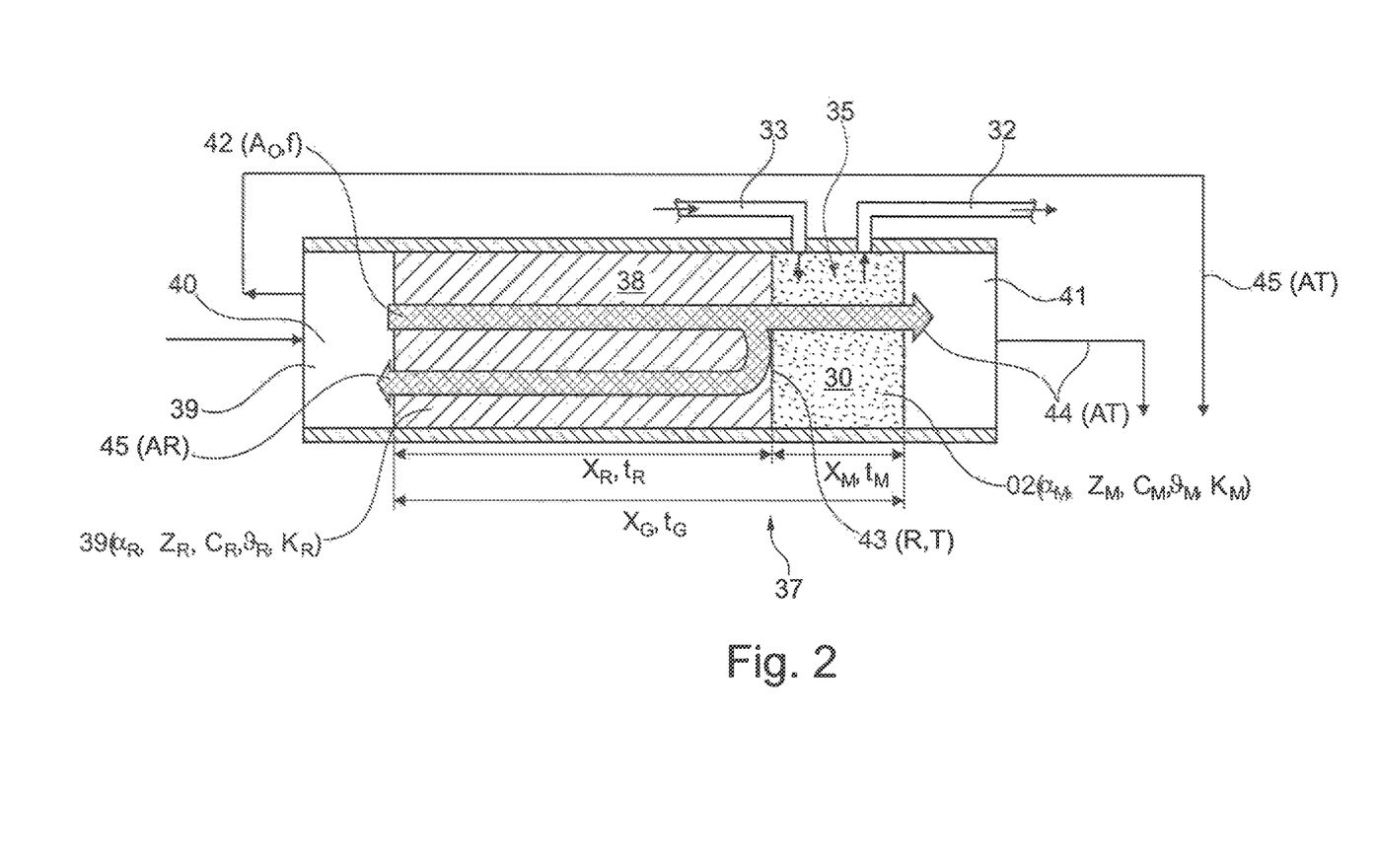
FIG. 2 illustrates the measuring distance of the device according to FIG. 1 in an enlarged view.

As schematically illustrated in FIG. 2, the ultrasonic transmission signal 42 first passes through the reference material 38 until it reaches the boundary surface 43 between the reference material 38 and the test material 02. A part of the ultrasonic transmission signal runs through the boundary surface 43 and passes through the test material 02 until it reaches the ultrasonic reception device 41 as a transmitted ultrasonic reception signal 44. By evaluating the transmitted ultrasonic reception signal 44, the time of flight $t_G$, which the transmitted ultrasonic reception signal has required for passing through the entire measuring distance 37, and the amplitude $A_T$ of the transmitted ultrasonic reception signal 44 can be measured or identified.

The portion of the ultrasonic reception signal 44 reflected on the boundary surface 43 passes through the reference material 38 a second time in the opposite direction until said portion reaches the ultrasonic reception device 40 realized by switching the ultrasonic transmission device 39 as a reflected ultrasonic reception signal 45. By evaluating the measuring values of the ultrasonic reception device 40, the amplitude $A_R$ of the reflected ultrasonic reception signal 45 can be identified. The manner in which the measuring signals of the two ultrasonic reception devices 41 are further processed is further described in the following by way of the sketch in FIG. 1.

Other than the combined ultrasonic transmission device and ultrasonic reception device 39/40 as well as the ultrasonic reception device 41, the device 01 comprises a signal preparation module 05 for generating the ultrasonic signals to be emitted from the ultrasonic transmission device 39. Further a signal generator 06 and a signal amplifier 07 are provided.

The signal paths recorded by the ultrasonic reception device 40 or 41 are first amplified using signal amplifiers 08. The transmitted ultrasonic reception signals 44 are subsequently split in a signal splitter 09 and are distributed to a first processing device 10 and a second processing device 11 for parallel processing. The first processing device 10 serves for determining the time of flight, which the transmitted ultrasonic reception signal 44 has required for passing through the measuring distance 37 for each correspondingly set frequency. After passing through a signal processing module 12, the transmitted ultrasonic reception signal 44 enters a time-to-digital converter 13, by means of which the time of flight of the ultrasonic signal, i.e. the time between emitting the signal from the ultrasonic transmission device 39 and receiving said transmitted ultrasonic reception signal 44 at the ultrasonic reception device 41, can be measured.

The functionality of the time-to-digital converter 13 is based upon the fact that the time of flight of an electric signal through a plurality of electronic circuits 14 contained in the time-to-digital converter 13 is known.

For measuring the time of flight, the trigger signal of the ultrasonic transmission signal is directed to the time-to-digital converter 13 simultaneously with the emission from the ultrasonic transmission device 39 in order to initiate the time-measuring process. The trigger signal of the ultrasonic transmission signal then passes through the consecutively arranged circuits 14 in the time-to-digital converter 13. Each passing through an electronic circuit 14, which corresponds to a predetermined time of flight, is added up by a counter 15. As soon as the ultrasonic reception signal 44 is directed to the electronic circuits 14, the counter 15 stops and multiplies the number of added passages by the known time of flight of the individual electronic circuits 14. The result is the overall time of flight $t_D$ for the corresponding measurement. A time of flight $(t_G)$ 16 is yielded for each transmission frequency and is stored with the corresponding allocated transmission frequency in a storage device 17 in each instance.

Parallel thereto, the transmitted ultrasonic reception signal 44 is evaluated in the second processing device 11 and the amplitude $A_T$ of the transmitted ultrasonic reception signal 20 is identified. For this purpose, a signal processing module 18 is provided in the second processing device 11, said transmitted ultrasonic reception signal 44 being processed and said amplitude $(A_T)$ 20 of the ultrasonic reception signal 44 being identified using said signal processing module 18. The ultrasonic reception signal 44 is split and indexed using the signal splitter 19. In a third processing device 46, the reflected ultrasonic reception signal 45 is processed by means of a signal processing module 18 and the amplitude ($A_R$) 47 of the reflected ultrasonic reception signal is identified. The amplitude values 20 and 47 are each identified in the processing devices 11 and 46 in a frequency-dependent manner and the results data are stored with the corresponding frequency in the storage device 17 in conjunction with the corresponding time of flight 16.

The results data stored in the storage device 17, namely the time of flight ($t_G$) 16, the amplitude ($A_T$) 20 of the transmitted ultrasonic reception signal 44 and the amplitude ($A_R$) 47 of the reflected ultrasonic reception signal 45, are subsequently read out from the storage device 17 and are forwarded to an evaluation device 48 for further calculating the results data.

Figure 3:
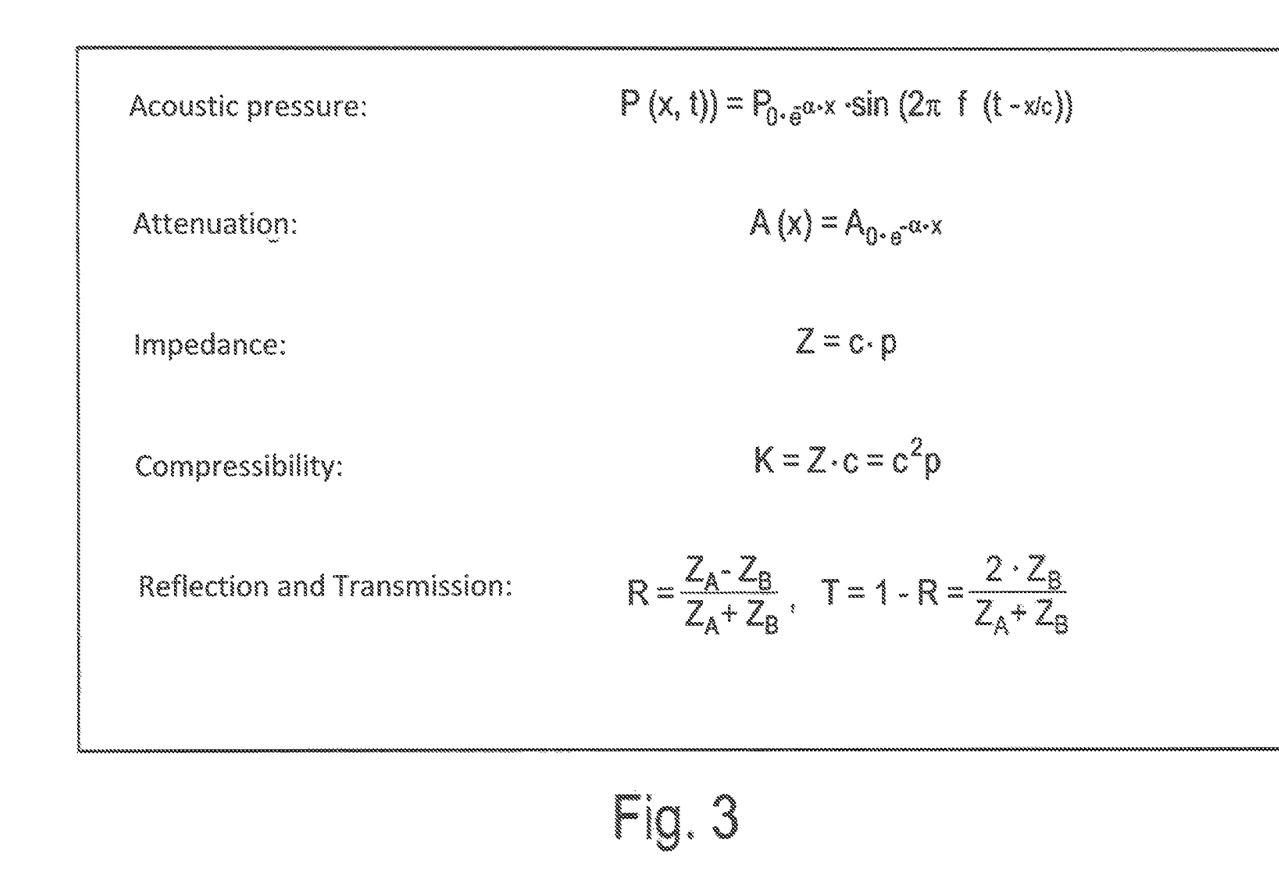
FIG. 3 illustrates the formulary for calculating the acoustic material parameters.

FIG. 3 shows the formulary for calculating acoustic material parameters as they are required by the evaluation device 48 for calculating the results data.

Figure 4:
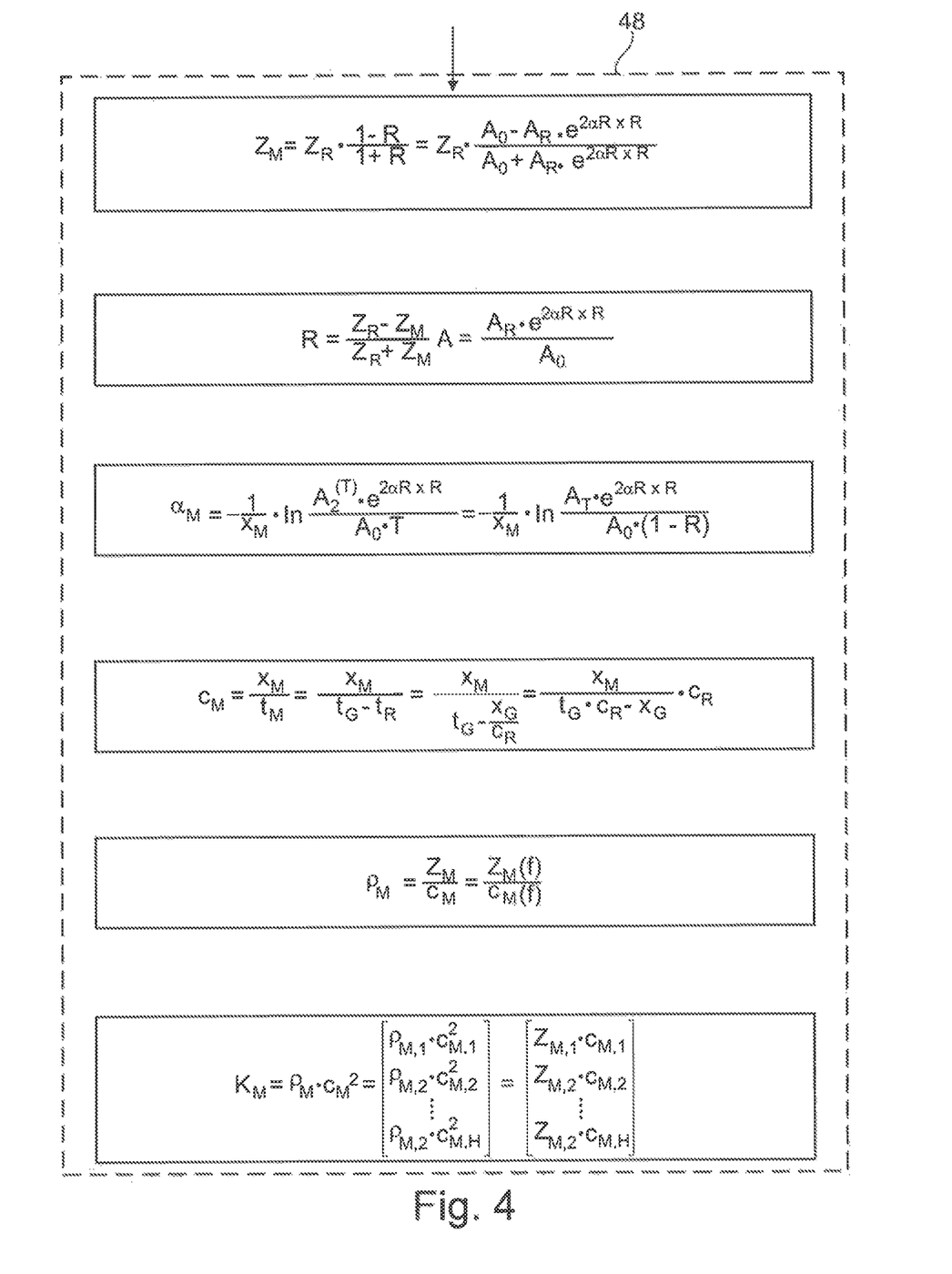
FIG. 4 illustrates the evaluation device of the device according to FIG. 1 having the formulas stored therein for calculating the acoustic material parameters of the test material to be examined.

FIG. 4 schematically illustrates the evaluation device 48, by means of which the results data for the acoustic impedance $Z_m$ of the test material, the degree of reflection R on the boundary surface 43, the acoustic attenuation coefficient $\alpha_M$ of the test material, the sonic transmission speed $c_M$ of the test material, the density $\rho_M$ of the test material and the compressibility of the test material can be calculated from the measuring values, namely the time of flight $t_G$, the amplitude ($A_T$) of the transmitted ultrasonic reception signal 24 and the amplitude ($A_R$) of the reflected reception signal 45, with the aid of the formulas shown in FIG. 4.

After determining the acoustic material parameters of the transformer oil 30 by calculation in the evaluation device 38, the water content or the acidity level can be determined in the transformer oil 30 in a subsequent step. Additionally, further insulation parameters, such as the breakdown voltage (according to BDV) as well as the dissipation factor (tangens delta), can be determined.

The invention claimed is:

1. A device for examining a test material via acoustic spectroscopy, comprising a measuring distance which is formed from a reference material and the test material, at least one of a density ($\rho_R$), a sonic transmission speed ($c_R$), an acoustic attenuation coefficient ($\alpha_R$) or an acoustic impedance ($Z_R$) of the acoustic material being known for different frequencies, and the length ($x_R$) of the reference material being known, and the length ($x_M$) of the test material being known, and comprising:

an ultrasonic transmission device for transmitting an ultrasonic transmission signal having an initial amplitude ($A_0$) through the measuring distance, configured for transmitting ultrasonic transmission signals having different frequencies (f);

a first ultrasonic reception device for receiving a transmitted ultrasonic reception signal after said transmitted ultrasonic signal has passed through the measuring distance;

a second ultrasonic reception device for receiving an ultrasonic reception signal reflected on a boundary surface between the test material and the reference material after said ultrasonic reception signal has twice passed through the reference material or the test material, the first and second reception devices being configured for receiving corresponding ultrasonic reception signals having different frequencies, a first processing device configured to measure a time of flight ($t_G$) of the transmitted ultrasonic reception signals after said signals have passed through the measuring distance, and a second processing device configured to identify an amplitude ($A_T$) of the transmitted ultrasonic reception signals after said transmitted ultrasonic reception signals have passed through the measuring distance, and a third processing device configured to identify an amplitude ($A_R$) of the ultrasonic reception signals reflected on the boundary surface between the test material and the reference material after said ultrasonic reception signals have twice passed through the reference material or the test material, and an evaluation device configured to calculate at least one of a density ($\rho_M$), a sonic transmission speed ($c_M$), an acoustic attenuation coefficient ($\alpha_M$) and/or an acoustic impedance ($Z_M$) of an acoustic material for different frequencies (f) from the time of flight ($t_G$), the amplitude ($A_T$) of the transmitted ultrasonic reception signal and/or the amplitude ($A_R$) of the reflected ultrasonic reception signal.

2. The device according to claim 1, wherein the time of flight ($t_G$) is identified with a resolution of at least 100 picoseconds in the first processing device.

3. The device according to claim 1 wherein the first processing device comprises a time-to-digital converter configured to identify the time of flight ($t_G$).

4. The device according to claim 1, wherein the second ultrasonic reception device is configured for receiving the ultrasonic reception signal reflected on the boundary surface between the test material and the reference material, after said ultrasonic reception signal has twice passed through the reference material or the test material, via switching the ultrasonic transmission device from a transmission mode to a reception mode.

5. The device according to claim 1, wherein the reference material consists of a solid body.

6. The device according to claim 1, wherein a cavity exists between the boundary surface of the reference material and the first ultrasonic reception device, a liquid or gaseous test material being able to fill or flow through said cavity during examination.

7. The device according to claim 1, wherein the device is connected to a container in which oil or an operating material is contained, said oil or operating material from the container filling or flowing through a cavity between the boundary surface of the reference material and the first ultrasonic reception device during examination, and at least one of the density ($\rho_M$), the sonic transmission speed ($c_M$), the acoustic attenuation coefficient ($\alpha_M$) or the acoustic impedance ($Z_M$) of the oil or the operating material being able to be identified.

8. The device according to claim 7, wherein the operating material comprises transformer oil, and wherein in the evaluation device, a water content and/or an acidity level in the transformer oil is derived from at least one of the density ($\rho_M$) of the transformer oil, the sonic transmission speed ($c_M$) in the transformer oil, the acoustic attenuation coefficient ($\alpha_M$) of the transformer oil or the acoustic impedance ($Z_M$) of the transformer oil.

9. A transformer for converting an AC input voltage to an AC output voltage, said transformer comprising a housing filled with transformer oil, wherein the device according to claim 1 is provided in or on the transformer for an online examination of the transformer oil.

10. A method for examining a biological or non-biological test material via acoustic spectroscopy, comprising a measuring distance which is formed from a reference material and the test material, at least one of a density ($\rho_R$), a sonic transmission speed ($c_R$), an acoustic attenuation coefficient ($\alpha_R$) and/or an acoustic impedance ($Z_R$) of an acoustic material being known for different frequencies, and a length ($x_R$) of the reference material being known, and a length ($x_M$) of the test material being known, and comprising the steps of:

transmitting an ultrasonic transmission signal having an initial amplitude ($A_0$) through the measuring distance using an ultrasonic transmission device, said transmission device being configured for transmitting ultrasonic transmission signals having different frequencies (f) into the measuring difference, and receiving the transmitted ultrasonic reception signal at a first ultrasonic reception device after said transmitted ultrasonic reception signal has passed through the measuring distance, and receiving an ultrasonic reception signal reflected on a boundary surface between the test material and the reference material at a second ultrasonic reception device after said ultrasonic reception signal has twice passed through the reference material or the test material, the first and second reception devices being configured for receiving corresponding ultrasonic reception signals having different frequencies (f), and a) measuring a time of flight ($t_G$) of the transmitted ultrasonic reception signals for each of the different ultrasonic transmission signals after said transmitted ultrasonic reception signals have passed through the measuring distance, b) identifying an amplitude ($A_T$) of the transmitted ultrasonic reception signals for the different ultrasonic transmission signals after said ultrasonic reception signals have passed through the measuring distance, c) identifying an amplitude ($A_R$) of the allocated ultrasonic reception signals reflected on the boundary surface between the test material and the reference material for the different ultrasonic transmission signals after said ultrasonic transmission signals have twice passed through the reference material or the test material, d) calculating at least one of a density ($\rho_M$), a sonic transmission speed ($c_M$), an acoustic attenuation coefficient ($\alpha_M$) or an acoustic impedance ($Z_M$) of the acoustic material, for different frequencies from the time of flight ($t_G$), the amplitude ($A_T$) of the transmitted ultrasonic reception signals or the amplitude ($A_R$) of the reflected ultrasonic reception signals.

11. The method according to claim 10, wherein the time of flight ($t_G$) is identified with a resolution of at least 100 picoseconds.

12. The method according to claim 10, wherein at least one of the density ($\rho_M$) of the transformer oil, the sonic transmission speed ($c_M$) in the transformer oil, the acoustic attenuation coefficient ($\alpha_M$) of the transformer oil or the acoustic impedance ($Z_M$) of the transformer oil are identified.

13. The method according to claim 12, wherein a water content or an acidity level in the transformer oil, is derived from at least one of the density ($\rho_M$) of the transformer oil, the sonic transmission speed ($c_M$) in the transformer oil, the acoustic attenuation coefficient ($\alpha_M$) of the transformer oil and/or the acoustic impedance ($Z_M$) of the transformer oil.

14. The method according to claim 10, wherein longitudinal ultrasonic waves are generated by the ultrasonic transmission device in the MHz range.

15. The method according to claim 10, wherein the ultrasonic transmission signals having different frequencies (f) are modulated onto or added to a shared carrier signal and are subsequently transmitted together in the ultrasonic transmission device.

16. The device according to claim 1, wherein the time of flight ($t_G$) is identified with a resolution of at least 10 picoseconds in the first processing device.

17. The device according to claim 1 wherein the reference material comprises at least one of plastic and glass.

18. The device according to claim 6, wherein the test material is transformer oil.

19. The method according to claim 10, wherein the time of flight ($t_G$) is identified with a resolution of at least 10 picoseconds.

* * * * *

UNITED STATES PATENT AND TRADEMARK OFFICE
CERTIFICATE OF CORRECTION

PATENT NO. : 10,613,057 B2
APPLICATION NO. : 15/743404
DATED : April 7, 2020
INVENTOR(S) : Krzysztof Fokow et al.

It is certified that error appears in the above-identified patent and that said Letters Patent is hereby corrected as shown below:

In the Specification

Column 6, Line 37, "oil, to a" should be --oil, a--.

Signed and Sealed this
Sixteenth Day of June, 2020

Andrei Iancu
*Director of the United States Patent and Trademark Office*